US007775970B2

(12) United States Patent
Maeda et al.

(10) Patent No.: US 7,775,970 B2
(45) Date of Patent: Aug. 17, 2010

(54) HARVESTING DEVICE FOR ENDOSCOPE

(75) Inventors: Seiji Maeda, Kunitachi (JP); Akihito Kano, Hachioji (JP)

(73) Assignee: Olympus Medical Systems Corp. (JP)

( * ) Notice: Subject to any disclaimer, the term of this patent is extended or adjusted under 35 U.S.C. 154(b) by 195 days.

(21) Appl. No.: 12/023,782

(22) Filed: Jan. 31, 2008

(65) Prior Publication Data

US 2009/0143641 A1    Jun. 4, 2009

Related U.S. Application Data

(63) Continuation of application No. PCT/JP2006/315155, filed on Jul. 31, 2006.

(30) Foreign Application Priority Data

Aug. 1, 2005    (JP) .............................. 2005-222732

(51) Int. Cl.
*A61B 1/00* (2006.01)
(52) U.S. Cl. .................. 600/106; 600/104; 600/107; 600/114; 600/127; 600/131; 600/146; 600/159; 606/144; 606/145; 606/159; 606/167
(58) Field of Classification Search ................ 600/118, 600/131, 146–148, 159
See application file for complete search history.

(56) References Cited

U.S. PATENT DOCUMENTS

| 3,145,249 | A | * | 8/1964 | Meltzer ...................... 359/508 |
| 5,518,502 | A | * | 5/1996 | Kaplan et al. ................ 600/157 |
| 5,928,264 | A | * | 7/1999 | Sugarbaker et al. .......... 606/207 |
| 5,954,731 | A | * | 9/1999 | Yoon ........................... 606/144 |
| 6,371,963 | B1 | | 4/2002 | Nishtala et al. |
| 6,406,425 | B1 | | 6/2002 | Chin et al. |
| 6,923,759 | B2 | | 8/2005 | Kasahara et al. |
| 7,331,971 | B2 | * | 2/2008 | Kasahara et al. ............. 606/159 |
| 2003/0130675 | A1 | * | 7/2003 | Kasahara et al. ............. 606/159 |

(Continued)

FOREIGN PATENT DOCUMENTS

JP    8-29699    2/1996

(Continued)

OTHER PUBLICATIONS

International Search Report dated Oct. 24, 2006 issued in corresponding PCT Application No. PCT/JP2006/315155.

(Continued)

*Primary Examiner*—Matthew J Kasztejna
(74) *Attorney, Agent, or Firm*—Ostrolenk Faber LLP

(57) ABSTRACT

A harvesting device for an endoscope includes a harvesting member inserted through an outer tube member, including a harvesting portion arranged at the distal end portion of the outer tube member and to perform a harvesting, and configured to move so that the harvesting member moves and positions the harvesting portion at a harvesting position and a standby position, a wipe member inserted through the outer tube member, including a wipe portion arranged at the distal end portion of the outer tube member, and configured to move so that the wipe member moves the wipe portion to wipe a distal end portion of the endoscope, and a conversion mechanism to convert the movement of the harvesting member into that of the wipe member to interlock the wiping of the wipe portion with the positioning of the harvesting portion.

3 Claims, 14 Drawing Sheets

U.S. PATENT DOCUMENTS

2004/0225183 A1 * 11/2004 Michlitsch et al. .......... 600/106

FOREIGN PATENT DOCUMENTS

| JP | 2003-199703 | 7/2003 |
| JP | 2003-199766 | 7/2003 |
| JP | 2003-310628 | 11/2003 |

OTHER PUBLICATIONS

Written Opinion dated Oct. 24, 2006 issued in corresponding PCT Application No. PCT/JP2006/315155.

English Translation of International Preliminary Report on Patentability and Written Opinion relating to International Appln No. PCT/JP2006/315155 dated Feb. 14, 2008.

* cited by examiner

HARVESTING DEVICE FOR ENDOSCOPE

CROSS REFERENCE TO RELATED APPLICATIONS

This is a Continuation Application of PCT Application No. PCT/JP2006/315155, filed Jul. 31, 2006, which was published under PCT Article 21(2) in Japanese.

This application is based upon and claims the benefit of priority from prior Japanese Patent Application No. 2005-222732, filed Aug. 1, 2005, the entire contents of which are incorporated herein by reference.

BACKGROUND OF THE INVENTION

1. Field of the Invention

The present invention relates to a harvesting device for an endoscope to be used in combination with the endoscope to perform a harvesting in a body cavity under observation with the endoscope.

2. Description of the Related Art

Heretofore, there has been used a harvesting device for an endoscope to perform a harvesting in a body cavity under observation with the endoscope. For example, in U.S. Pat. No. 6,371,963, a puncture needle device for an endoscope is disclosed. In this puncture needle device for the endoscope, a puncture needle and a wire are inserted through a catheter sheath, and a distal end portion of the puncture needle and a loop arranged at a distal end portion of the wire are configured to protrude from a distal end portion of the catheter sheath. In this puncture needle device for the endoscope, when a handle on a hand side is operated to move one of the puncture needle and the wire forward or backward, the other of them automatically move backward or forward, so that when one of the puncture needle distal end portion and the loop is protruded, the other of them is automatically received therein.

Moreover, in Jpn. Pat. Appln. KOKAI Publication No. 2003-199703, a sheath for an endoscope is disclosed, through which the endoscope is inserted, for use mainly in an operation to drag and sample a great saphenous vein hypodermic blood vessel. This sheath for the endoscope is provided with a harvesting mechanism such as a high-frequency accessory for harvesting a tissue. Here, when the endoscope is inserted into the body cavity and pushed forward to a target region, mucosa, blood, subcutaneous fat and the like in the body cavity attach to an objective lens surface of a distal end portion of the endoscope sometimes. In addition, when the tissue is harvested with the high-frequency accessory, smoke, mist, separated tissue and the like generated by cautery of the tissue attach to the objective lens surface sometimes. Such attached matter disturbs a view field of the endoscope, and therefore needs to be removed. The sheath for the endoscope disclosed in Jpn. Pat. Appln. KOKAI Publication No. 2003-199703 is provided with a wipe mechanism for wiping the objective lens of the endoscope, independently of the harvesting mechanism for harvesting the tissue.

BRIEF SUMMARY OF THE INVENTION

In an aspect of the present invention, a harvesting device for an endoscope includes: an elongated outer tube member through which an endoscope is to be inserted and including a distal end portion where a distal end portion of the endoscope is to be arranged and a proximal end portion where a proximal end portion of the endoscope is to be arranged; a harvesting member inserted through the outer tube member, including a harvesting portion arranged at the distal end portion of the outer tube member and to perform a harvesting, and configured to move so that the harvesting member moves and positions the harvesting portion at a harvesting position where the harvesting portion is to be perform the harvesting and a standby position where the harvesting portion is to be perform no harvesting; an operating portion to move the harvesting member to perform the positioning of the harvesting portion; a wipe member inserted through the outer tube member, including a wipe portion arranged at the distal end portion of the outer tube member, and configured to move so that the wipe member moves the wipe portion to wipe the distal end portion of the endoscope; and a conversion mechanism to convert the movement of the harvesting member into that of the wipe member to interlock the wiping of the wipe portion with the positioning of the harvesting portion.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
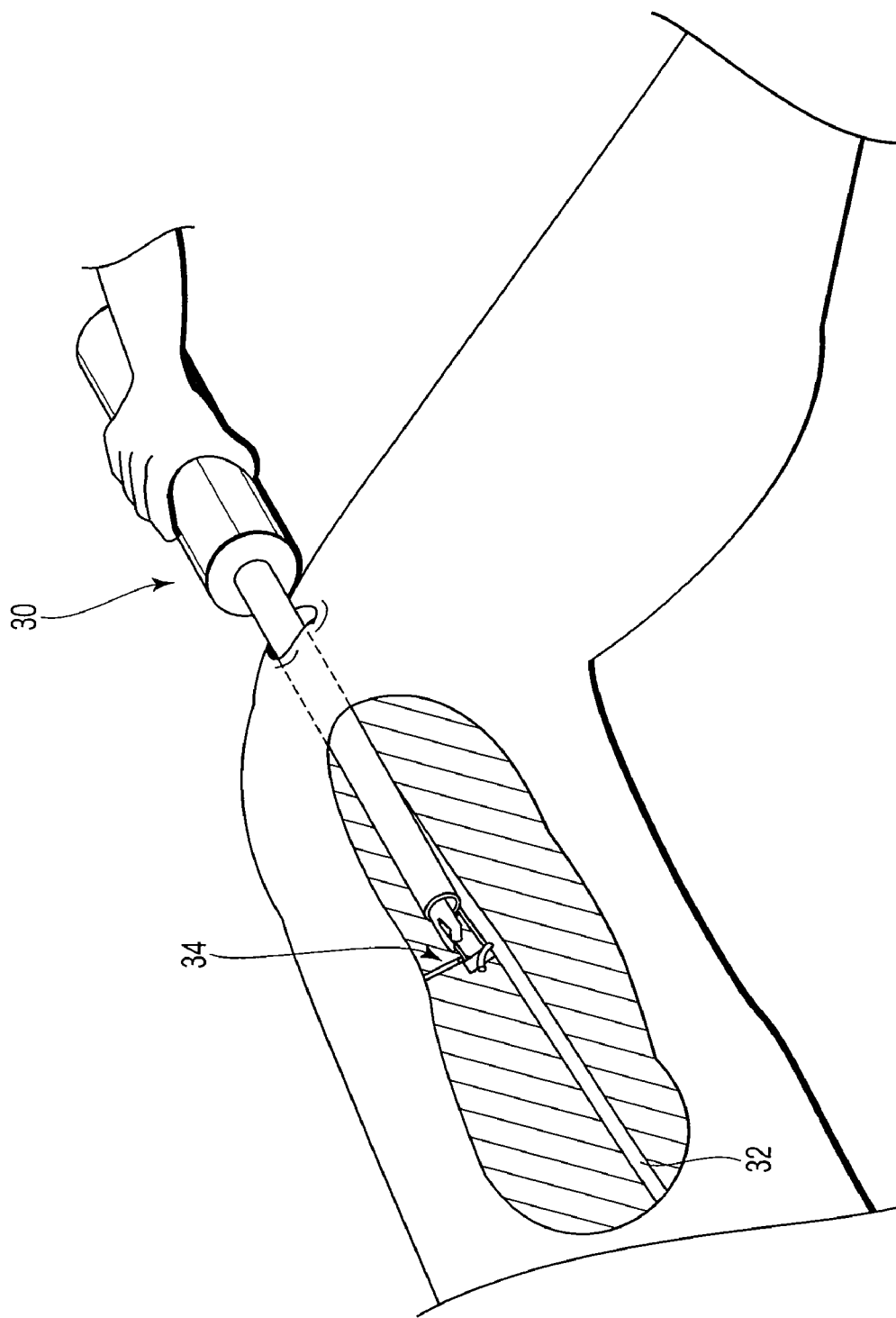
FIG. 1 is a perspective view showing a harvesting device for an endoscope and an endoscope in a use state according to a first embodiment of the present invention.

A first embodiment of the present invention will hereinafter be described with reference to FIGS. 1 to 8. As shown in FIG. 1, a harvesting device 30 for an endoscope of the present embodiment is used for cutting a side branch blood vessel 34 from a main blood vessel 32 in order to sample the main blood vessel 32, and may be used whether the main blood vessel 32 is an artery or a vein.

Figure 2:
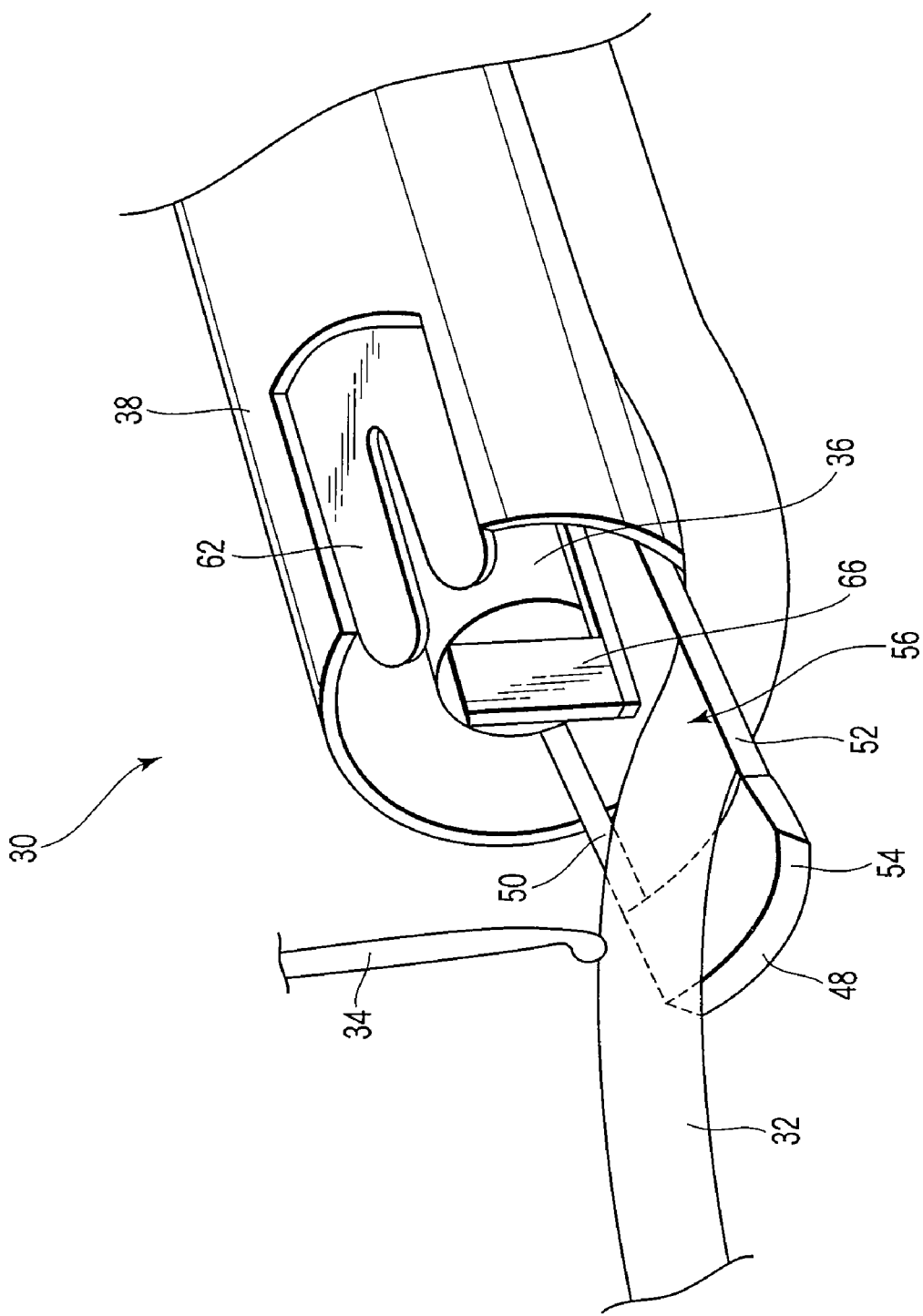
FIG. 2 is a perspective view showing distal end portions of the harvesting device for the endoscope and the endoscope according to the first embodiment of the present invention.
Figure 3:
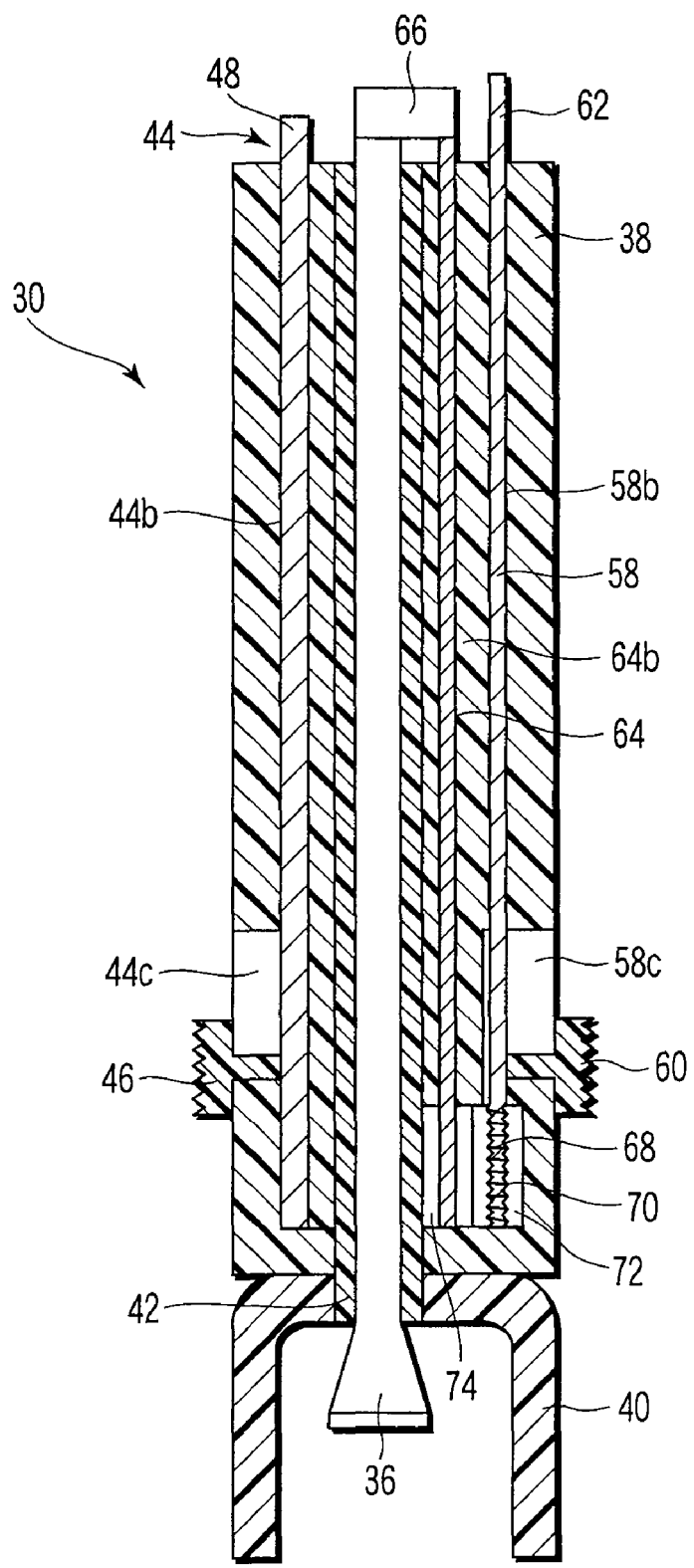
FIG. 3 is a longitudinal sectional view showing the harvesting device for the endoscope and the endoscope in a state in which a cutting portion is disposed at a standby position according to the first embodiment of the present invention.
Figure 4:
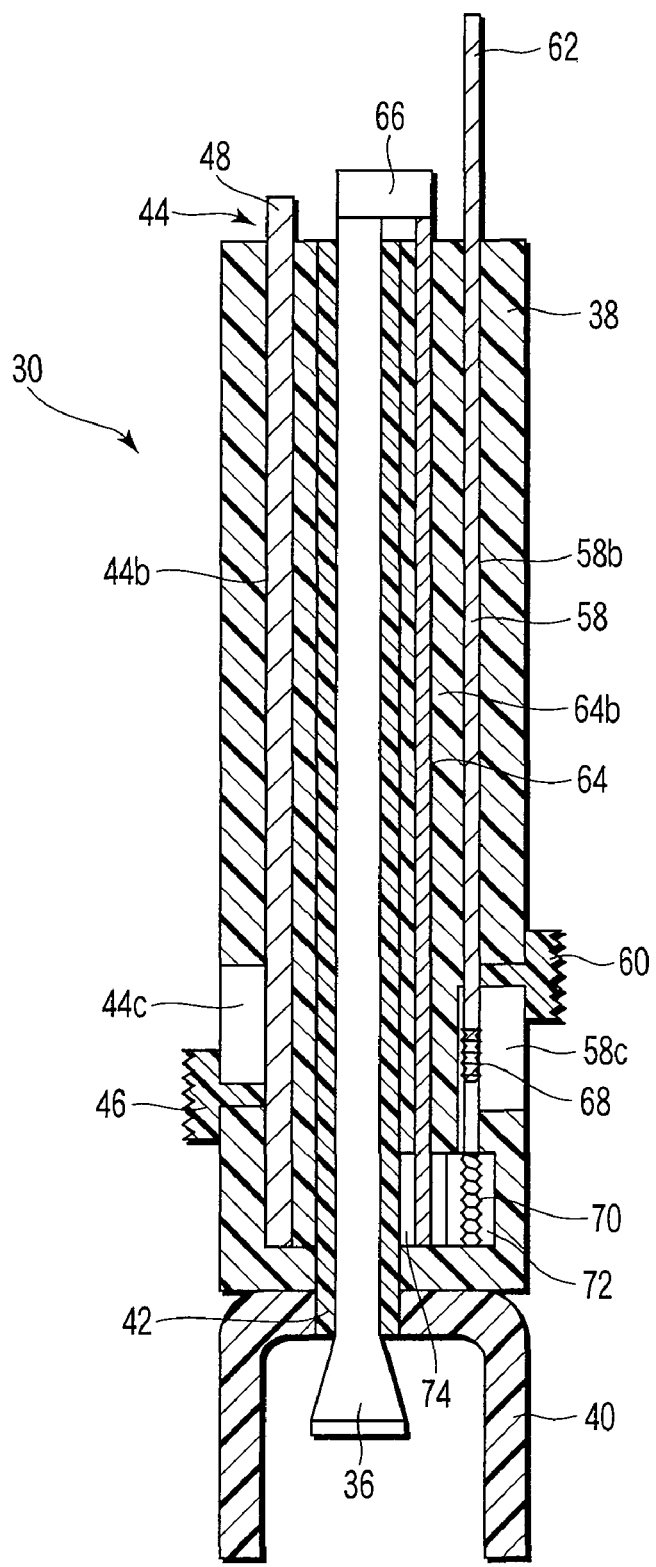
FIG. 4 is a longitudinal sectional view showing the harvesting device for the endoscope and the endoscope in a state in which the cutting portion is disposed at a cutting position according to the first embodiment of the present invention.

As shown in FIGS. 2 and 3, an endoscope 36 is to be detachably inserted through the harvesting device 30 for the endoscope of the present embodiment. That is, the harvesting device 30 for the endoscope includes an outer tube member 38, and a proximal end portion of this outer tube member 38 is provided with an endoscope holding member 40. In the outer tube member 38 and endoscope holding member 40, an endoscope introduction tube 42 is extended from the proximal end portion to a distal end portion. The endoscope 36 is to be slidably inserted through the endoscope introduction tube 42, a proximal end portion of the endoscope 36 is to be detachably held by the endoscope holding member 40, and therefore the endoscope 36 is to be detachably inserted through the harvesting device 30 for the endoscope. Moreover, when the endoscope 36 is attached to the harvesting device 30 for the endoscope, a distal end portion of the endoscope 36 protrudes an amount from a distal end portion of the harvesting device 30 for the endoscope.

Moreover, the harvesting device 30 for the endoscope includes a holding mechanism for taking the main blood vessel 32 to hold the side branch blood vessel 34. That is, in the outer tube member 38, a holding member channel 44b is formed to extend from the proximal end portion to the distal end portion, and a holding member 44 is inserted through the holding member channel 44b and configured to move forward and backward. A proximal end portion of the holding member 44 is connected to a holding member operating portion 46 via a holding member slit 44c extended in a longitudinal axis direction of the harvesting device 30 for the endoscope in the proximal end portion of the outer tube member 38. This holding member operating portion 46 is configured to move forward and backward in the longitudinal axis direction, and through the forward and backward movement of the holding member operating portion 46 in the above longitudinal axis direction, the holding member 44 moves forward and backward. Furthermore, a distal end portion of the holding member 44 is configured to protrude from a distal end portion of the outer tube member 38.

The distal end portion of the holding member 44 is provided with a holding portion 48 to take the main blood vessel 32 to hold the side branch blood vessel 34. This holding portion 48 includes a fixed shaft 50 and a holding portion shaft 52 arranged in parallel with each other in the longitudinal axis direction, and distal end portions of these fixed shaft 50 and holding portion shaft 52 are provided with a substantially rectangular thin-plate-like holding portion distal member 54. Moreover, the fixed shaft 50, the holding portion shaft 52 and the holding portion distal member 54 define a take-in opening 56 to take the main blood vessel 32. Furthermore, the holding portion shaft 52 is configured to move forward and backward in the longitudinal axis direction, and the distal end portion of the holding portion shaft 52 is configured to move between a closed position in which the distal end portion is locked with the holding portion distal member 54 to bring one side portion of the take-in opening 56 into a closed state and an opened position in which the distal end portion is maximally moved to a proximal side to bring the one side portion of the take-in opening 56 into an opened state. It is to be noted that the holding portion shaft 52 is configured to move forward and backward by a holding portion shaft operating portion arranged at a proximal end portion of the harvesting device 30 for the endoscope.

Moreover, the harvesting device 30 for the endoscope includes a cutting mechanism for cutting the side branch blood vessel 34 from the main blood vessel 32. The cutting mechanism includes a cutting member channel 58*b*, a cutting member 58 as a harvesting member, a cutting member slit 58*c*, and a cutting member operating portion 60 having configurations similar to those of the holding member channel 44*b*, the holding member 44 and the holding member slit 44*c*, the holding member operating portion 46, of the holding mechanism. However, a distal end portion of the cutting member 58 is provided with a cutting portion 62 as a harvesting portion to cut the side branch blood vessel 34 from the main blood vessel 32. The cutting portion 62 of the present embodiment is configured to cauterize and cut a tissue by use of a bipolar high-frequency current. Then, the cutting member 58 is configured to move forward and backward to move the cutting portion 62 between a standby position (see FIG. 3) on a proximal side where the cutting portion 62 is to perform no cutting and a cutting position (see FIG. 4) as a harvesting position on a distal side where the cutting portion 62 is to perform the cutting.

Furthermore, the harvesting device 30 for the endoscope includes a wipe mechanism for wiping an objective lens surface of the distal end portion of the endoscope 36 attached to the harvesting device 30 for the endoscope. That is, in the outer tube member 38, a wipe member channel 64*b* is formed to extend from the proximal end portion to the distal end portion, and a wipe member 64 is inserted through this wipe channel and configured to rotate around a central axis of itself. A distal end portion of this wipe member 64 protrudes from the distal end portion of the harvesting device 30 for the endoscope, and the distal end portion of the wipe member 64 is provided with a wiper-like wipe portion 66 to wipe the objective lens surface. That is, through the rotation of the wipe member 64 around the central axis, the wipe portion 66 crosses the objective lens surface while being pressed on the objective lens surface, and the objective lens surface is wiped.

In addition, the harvesting device 30 for the endoscope includes a conversion mechanism for converting the forward and backward movement of the cutting member 58 into the rotation of the wipe member 64. That is, in a proximal end portion of the cutting member 58, an external thread portion 68 is formed in the longitudinal axis direction. This external thread portion 68 is engaged with an internal thread portion 70 formed at an inner peripheral surface of a cylindrical first gear 72. The first gear 72 is extended in the longitudinal axis direction and configured to rotate around the central axis of itself. Then, through the engagement and interaction between the external thread portion 68 of the cutting member 58 and the internal thread portion 70 of the first gear 72 caused by the forward and backward movement of the cutting member 58 in the longitudinal axis direction, the first gear 72 is rotated around the central axis of itself. A tooth portion of an outer peripheral surface of the first gear 72 is engaged with that of an outer peripheral surface of a cylindrical second gear 74. This second gear 74 is extended in the longitudinal axis direction and configured to rotate around a central axis of itself. Moreover, the second gear 74 is coaxially connected to the wipe member 64. That is, through the rotation of the second gear 74 around the central axis of itself by the first gear 72, the wipe member 64 is rotated around the central axis of itself, and the objective lens surface of the endoscope 36 is wiped by the wipe portion 66.

It is to be noted that when the cutting member 58 is disposed at a proximal end, the external thread portion 68 of the cutting member 58 is maximally engaged with the internal thread portion 70 of the first gear 72. When the cutting member 58 moves forward from the proximal side to the distal side, the engagement between the external thread portion 68 and the internal thread portion 70 is released before the cutting member 58 reaches a distal end. The position of the cutting portion 62 where engagement is released will hereinafter be referred to as a released position. That is, when the cutting portion 62 is disposed between the standby position and the released position, the cutting member 58 interlocks with the wipe member 64. When the cutting portion 62 is disposed between the released position and the cutting position, the cutting member 58 moves independently of the wipe member 64.

Next, an operation of the harvesting device 30 for the endoscope of the present embodiment will be described. In the following operation, for example, while the proximal end portion of the harvesting device 30 for the endoscope is held with one hand, the cutting member operating portion 60 is operated with a thumb, and a holding portion shaft operating portion and the holding member operating portion 46 are operated with fingers.

Figure 5A:
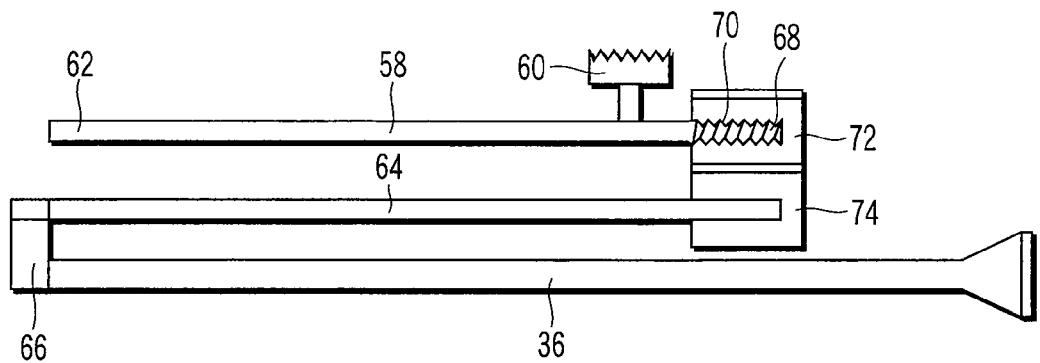
FIG. 5A is a schematic diagram showing the harvesting device for the endoscope and the endoscope in the state in which the cutting portion is disposed at the standby position according to the first embodiment of the present invention.
Figure 5B:
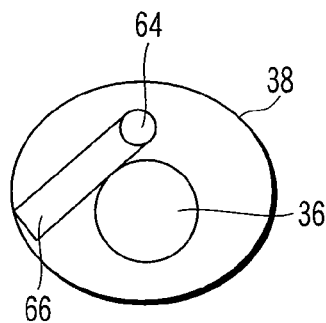
FIG. 5B is a front view showing the harvesting device for the endoscope and the endoscope in the state in which the cutting portion is disposed at the standby position according to the first embodiment of the present invention.
Figure 7:
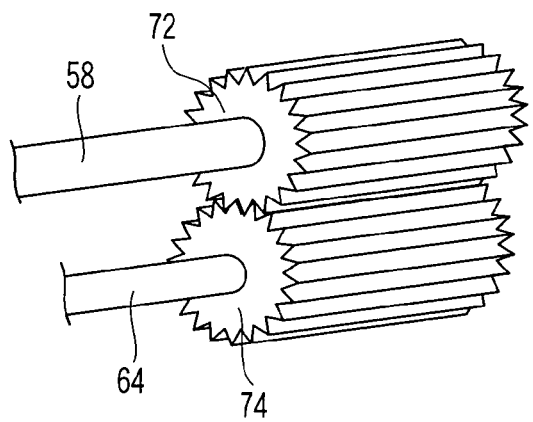
FIG. 7 is a schematic diagram showing a conversion mechanism of the harvesting device for the endoscope in the state in which the cutting portion is disposed at the standby position according to the first embodiment of the present invention.

To perform a cutting of the side branch blood vessel 34 by use of the harvesting device 30 for the endoscope, as shown in FIGS. 5A, 5B and 7, the endoscope 36 is inserted through the harvesting device 30 for the endoscope, the cutting member operating portion 60 is arranged at a proximal end, and the cutting portion 62 is previously positioned at the standby position. Then, the endoscope 36 and the harvesting device 30 for the endoscope are inserted into a body cavity, and the distal end portions of the endoscope 36 and the harvesting device 30 for the endoscope is pushed forward to a target region.

Figure 6A:
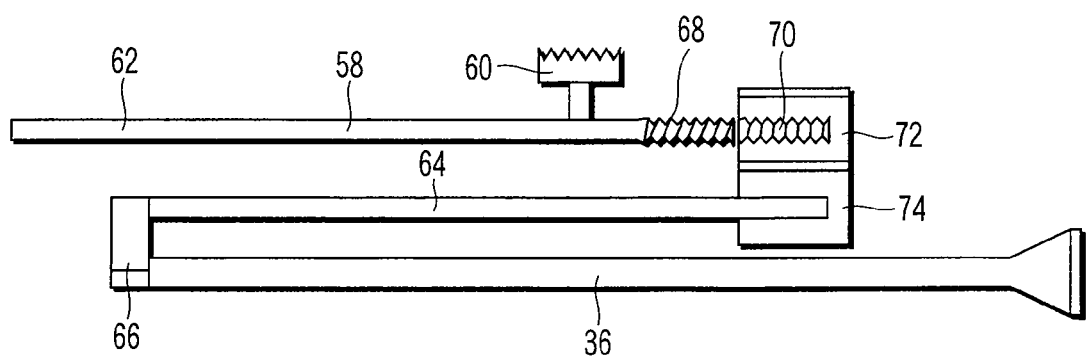
FIG. 6A is a schematic diagram showing the harvesting device for the endoscope and the endoscope in a state in which the cutting portion is disposed at a released position according to the first embodiment of the present invention.
Figure 6B:
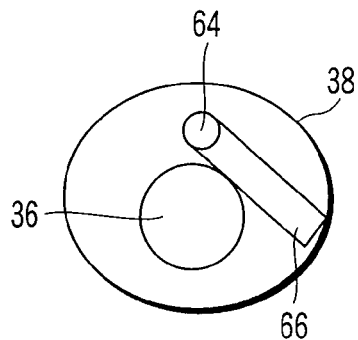
FIG. 6B is a front view showing the harvesting device for the endoscope and the endoscope in the state in which the cutting portion is disposed at the released position according to the first embodiment of the present invention.
Figure 8:
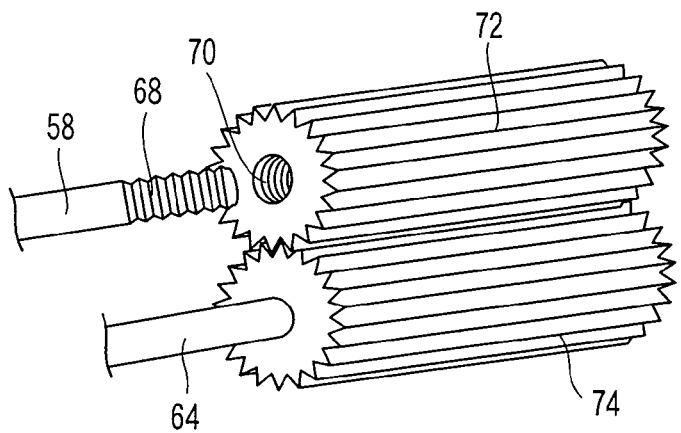
FIG. 8 is a schematic diagram showing the conversion mechanism of the harvesting device for the endoscope in the state in which the cutting portion is disposed at the released position according to the first embodiment of the present invention.

After pushing the distal end portions of the endoscope 36 and the harvesting device 30 for the endoscope forward to the target region, as shown in FIGS. 6A, 6B and 8, the cutting member operating portion 60 is moved forward from the proximal end to a distal end, and the cutting portion 62 is moved from the standby position to the released position. In this case, the forward movement of the cutting member 58 is converted into the rotation of the wipe member 64 in one direction by the external thread portion 68, the internal thread portion 70 and the first and second gears 74, and the objective lens surface of the endoscope 36 is wiped by the wipe portion 66 at the distal end portion of the wipe member 64 at least once. Here, when the distal end portion of the endoscope 36 is pushed forward to the target region, mucosa, blood, subcutaneous fat and the like in the body cavity sometimes attach to the objective lens surface, but such attached matter is wiped by the wiping of the wipe portion 66 interlocked with the positioning of the cutting portion 62, and a satisfactory view field of the endoscope 36 is secured.

A cutting operation of the side branch blood vessel 34 is performed under observation with the endoscope. First, the holding member operating portion 46 is operated to protrude the holding portion 48 from the harvesting device 30 for the endoscope, and the holding portion shaft 52 is moved backward to the proximal side to bring one side portion of the take-in opening 56 into the opened state. Then, the holding member operating portion 46 is operated to catch the main blood vessel 32 in the take-in opening 56, and the holding portion shaft 52 is moved forward to the distal side to bring the one side portion of the take-in opening 56 into the closed state, whereby the main blood vessel 32 is taken into the take-in opening 56. Then, the holding member operating portion 46 is operated to move the holding portion 48 forward and backward, the side branch blood vessel 34 is caught and applied a tension to by the holding portion 48, and the side branch blood vessel 34 is held by the holding portion 48. Afterward, the cutting member operating portion 60 is operated to move the cutting portion 62 forward from the released position and abut the cutting portion 62 on the side branch blood vessel 34, and the side branch blood vessel 34 is cauterized and cut from the main blood vessel 32 by the cutting portion 62. In this case, the engagement between the external thread portion 68 and the internal thread portion 70 is being released, hence the forward and backward movement of the cutting member 58 are not converted into the rotation of the wipe member 64, and the cutting portion 62 is operated between the released position and the cutting position independently of the wipe portion 66.

After cutting the side branch blood vessel 34 from the main blood vessel 32, the cutting member operating portion 60 is moved backward from the distal end to the proximal end. When the cutting portion 62 is moved from the released position to the standby position, the backward movement of the cutting member 58 is converted into the rotation of the wipe member 64 in the other direction by the external thread portion 68, the internal thread portion 70, and the first and second gears 74, and the objective lens surface of the endoscope 36 is wiped by the wipe portion 66 at the distal end portion of the wipe member 64 at least once. Here, when the side branch blood vessel 34 is cut from the main blood vessel 32 by the cutting portion 62, smoke, mist, separated tissue and the like generated by cautery of the tissue sometimes attach to the objective lens surface. However, such attached matter is wiped off by the wiping of the wipe portion 66 interlocked with the positioning of the cutting portion 62, and the satisfactory view field of the endoscope 36 is secured. Afterward, the side branch blood vessel 34 is successively cut from the main blood vessel 32 so that the main blood vessel 32 can be sampled.

Therefore, the harvesting device 30 for the endoscope of the present embodiment produces the following effect. In the harvesting device 30 for the endoscope of the present embodiment, in order to cut the side branch blood vessel 34, when the cutting member operating portion 60 is operated to move the cutting member 58 forward and the cutting portion 62 is positioned from the standby position to the cutting position, the forward movement of the cutting member 58 is converted into the rotation of the wipe member 64 in one direction by the conversion mechanism, whereby the distal end portion of the endoscope 36 is wiped by the wipe portion 66. After the side branch blood vessel 34 is cut, the cutting member operating portion 60 is operated to move the cutting member 58 backward and the cutting portion 62 is positioned from the released position to the standby position, the backward movement of the cutting member 58 is converted into the rotation of the wipe member 64 in the other direction by the conversion mechanism, whereby the distal end portion of the endoscope 36 is wiped by the wipe portion 66. Thus, in the present embodiment, when the cutting member operating portion 60 is operated to cut the side branch blood vessel 34, the objective lens surface of the endoscope 36 is automatically wiped, and therefore the convenience of the harvesting device 30 for the endoscope is improved.

Moreover, the cutting portion 62 is configured to move between the standby position and the cutting position, and between the released position and the cutting position, the forward and backward movement of the cutting member 58 are not converted into the rotation of the wipe member 64 by the conversion mechanism, and the cutting portion 62 is operated independently of the wipe portion 66. Therefore, unnecessary wiping is avoided, and an operation force necessary for the forward and backward movement of the cutting portion 62 in performing the cutting by the cutting portion 62 is reduced, so that the convenience of the harvesting device 30 for the endoscope is further improved.

Figure 9:
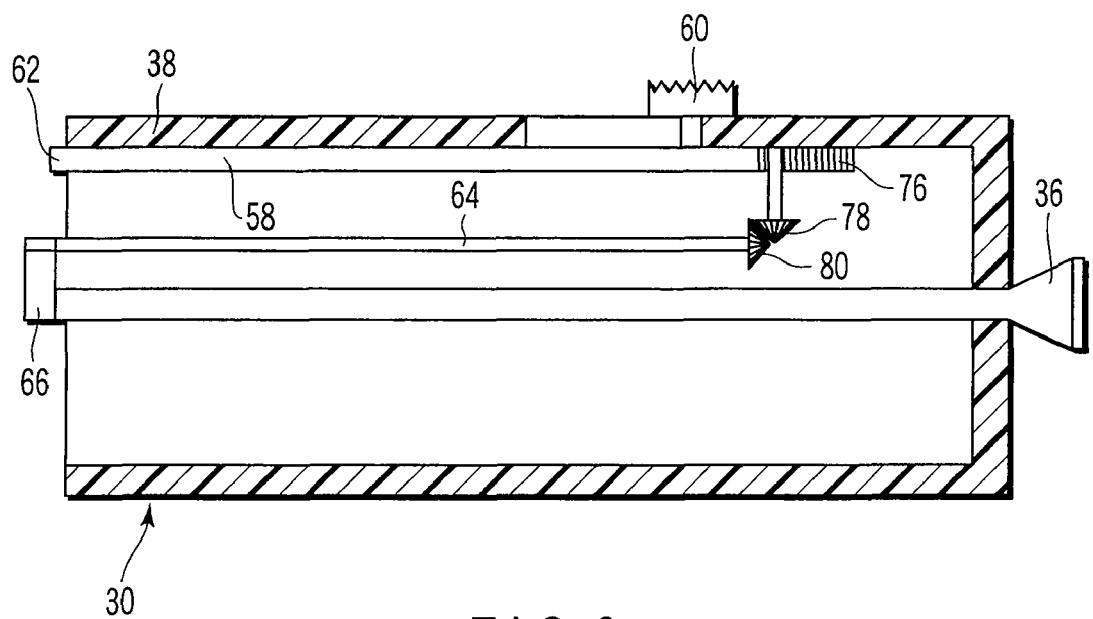
FIG. 9 is a schematic diagram showing a harvesting device for an endoscope and an endoscope in a state in which a cutting portion is disposed at a standby position according to a second embodiment of the present invention.
Figure 10:
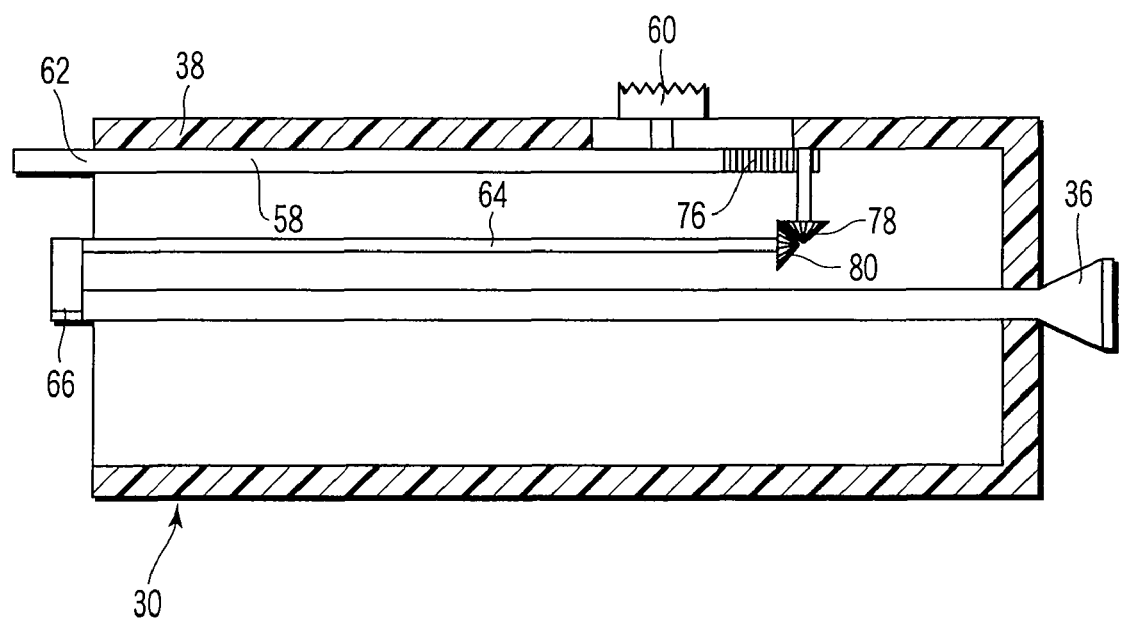
FIG. 10 is a schematic diagram showing the harvesting device for the endoscope and the endoscope in a state in which the cutting portion is disposed at a released position according to the second embodiment of the present invention.

FIGS. 9 and 10 show a second embodiment of the present invention. A component having a function similar to that of the first embodiment is denoted with the same reference numerals, and description thereof is omitted. As shown in FIG. 9, in the harvesting device 30 for the endoscope of the present embodiment, a rack portion 76 and first and second bevel gears 78, 80 form the conversion mechanism for converting the forward and backward movement of the cutting member 58 into the rotation of the wipe member 64.

That is, in the proximal end portion of the cutting member 58 of the harvesting device 30 for the endoscope, the rack portion 76 extends in the longitudinal axis direction of the harvesting device 30 for the endoscope. This rack portion 76 is engaged with a shaft portion of the first bevel gear 78. This first bevel gear 78 is arranged to be substantially perpendicular to the forward and backward movement direction of the rack portion 76, and is configured to rotate around a central axis of itself. That is, through the forward and backward movement of the rack portion 76 in the longitudinal axis direction, the first bevel gear 78 is rotated around the central axis of itself. A tooth portion of this first bevel gear 78 is engaged with that of the second bevel gear 80. This second bevel gear 80 is coaxially connected to the proximal end portion of the wipe member 64. That is, when the second bevel gear 80 is rotated around the central axis of itself by the first bevel gear 78, the wipe member 64 is rotated around the central axis of itself.

It is to be noted that when the cutting member 58 is disposed at the proximal end, a distal end portion of the rack portion 76 of the cutting member 58 engages with the shaft portion of the first bevel gear 78. When the cutting member 58 is moved forward from the proximal side to the distal side, as shown in FIG. 10, the engagement between the rack portion 76 and the shaft portion of the first bevel gear 78 is released before the cutting member 58 reaches the distal end. The position of the cutting portion 62 where the engagement is released is the released position.

Next, an operation of the harvesting device 30 for the endoscope of the present embodiment will be described. When the cutting portion 62 is moved between the standby position and the released position, the forward and backward movement of the cutting member 58 are converted into the rotation of the wipe member 64 by the rack portion 76 and the first and second bevel gears 78, 80, and the objective lens surface of the endoscope 36 is wiped by the wipe portion 66 at the distal end portion of the wipe member 64. Moreover, the cutting portion 62 is moved between the standby position and the cutting position, and the engagement between the rack portion 76 and the shaft portion of the first bevel gear 78 is being released between the released position and the cutting position. Therefore, the forward and backward movement of the cutting member 58 is not converted into the rotation of the wipe member 64, and the cutting portion 62 is operated independently of the wipe portion 66.

Therefore, the harvesting device 30 for the endoscope of the present embodiment produces an effect similar to that of the harvesting device 30 for the endoscope of the first embodiment.

Figure 11:
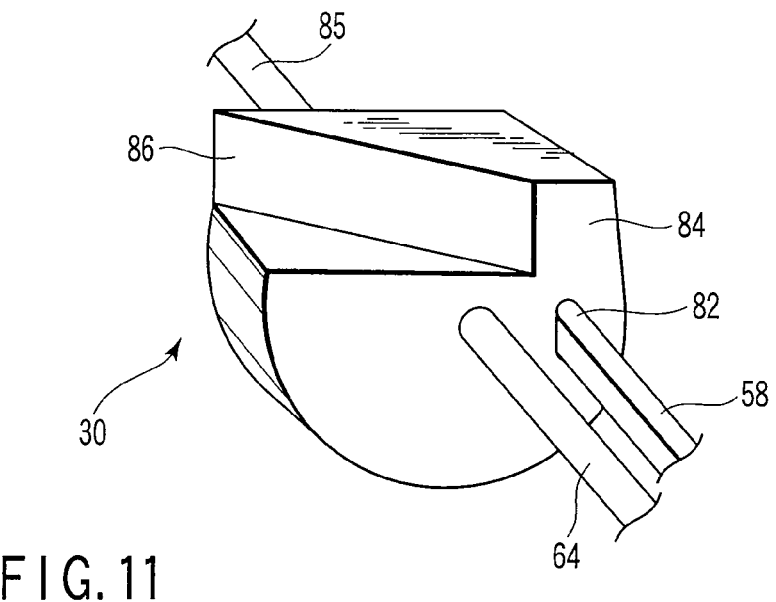
FIG. 11 is a perspective view showing a conversion mechanism of a harvesting device for an endoscope according to a third embodiment of the present invention.
Figure 12:
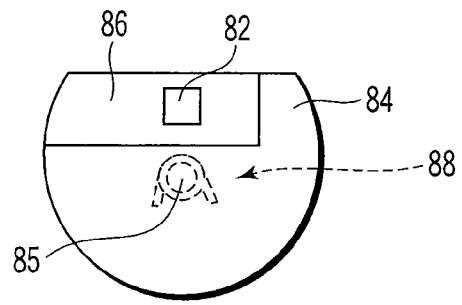
FIG. 12 is a front view showing the conversion mechanism of the harvesting device for the endoscope in a state in which a cutting portion is disposed at a released position according to the third embodiment of the present invention.
Figure 13:
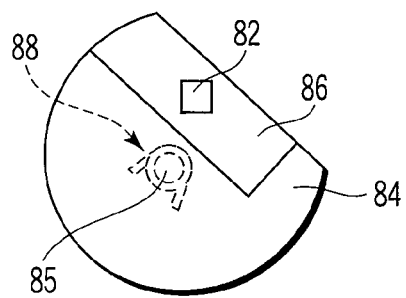
FIG. 13 is a front view showing the conversion mechanism of the harvesting device for the endoscope in a state in which the cutting portion is disposed at a standby position according to the third embodiment of the present invention.

FIGS. 11 to 13 show a third embodiment of the present invention. A component having a function similar to that of the first embodiment is denoted with the same reference numerals, and description thereof is omitted. As shown in FIG. 11, in the harvesting device 30 for an endoscope of the present embodiment, a cam mechanism formed by a pressing portion 82 and a cam member 84 forms a conversion mechanism for converting the forward and backward movement of the cutting member 58 into the rotation of the wipe member 64.

That is, the cam member 84 is connected to the proximal end portion of the wipe member 64 of the harvesting device 30 for the endoscope. A proximal end portion of this cam member 84 is connected pivotally to a shaft member 85 which is coaxial with the wipe member 64, and the wipe member 64 and the cam member 84 are configured to integrally rotate around the central axis of the wipe member 64. A distal surface of the cam member 84 is provided with a cam slope 86. On the other hand, the proximal end portion of the cutting member 58 is provided with the pressing portion 82. When the cutting member 58 is moved backward from the distal end to the proximal end, this pressing portion 82 presses the cam slope 86 of the cam member 84, and is slid along the cam slope 86 while rotating the cam member 84. This rotation of the cam member 84 causes the wipe member 64 to rotate.

Then, as shown in FIGS. 11 to 13, an urging member 88 having a wound spring configuration is provided around the shaft member 85, and one end and the other end of the urging member 88 are fixed to the shaft member 85 and the cam member 84, respectively. Then, the urging member 88 urges the cam member 84 in a direction reverse to the rotation direction through the press of the pressing portion 82. Therefore, when the cutting member 58 is moved forward from the proximal end to the distal end, through the urging of the urging member 88, the cam member 84 follows the pressing portion 82 to rotate while abutting the cam slope 86 on the pressing portion 82. Through this rotation of the cam member 84, the wipe member 64 is rotated in a direction reverse to the rotation direction through the press of the pressing portion 82.

It is to be noted that when the cutting member 58 is disposed at the proximal end, the pressing portion 82 is engaged with the cam slope 86, and the cam member 84 is maximally rotated. When the cutting member 58 is moved forward from the proximal side to the distal side, the abutment of the cam slope 86 on the pressing portion 82 is released before the cutting member 58 reaches the distal end. The position of the cutting portion 62 (see FIG. 6A, etc.) where the engagement is released is the released position.

Next, an operation of the harvesting device 30 for the endoscope of the present embodiment will be described. When the cutting portion 62 is moved between the standby position and the released position, the forward and backward movement of the cutting member 58 is converted into the rotation of the wipe member 64 by the pressing portion 82 and the cam member 84. Moreover, between the released position and the cutting position, the engagement between the pressing portion 82 and the cam slope 86 is released, so that the cutting portion 62 is operated independently of the wipe portion 66.

Therefore, the harvesting device 30 for the endoscope of the present embodiment produces an effect similar to that of the harvesting device 30 for the endoscope of the first embodiment.

FIGS. 14 to 16B show a first reference embodiment of the present invention. A component having a function similar to that of the first embodiment is denoted with the same reference numerals, and description thereof is omitted.

In the first embodiment, when the main blood vessel 32 is taken by the holding portion 48, the holding portion shaft 52 is moved backward to the proximal side to bring one side portion of the take-in opening 56 into the opened state, the holding member operating portion 46 is operated to catch the main blood vessel 32 into the take-in opening 56, and the holding portion shaft 52 is moved forward to the distal side to bring the one side portion of the take-in opening 56 into the closed state, thereby taking the main blood vessel 32 into the take-in opening 56. However, such the take-in operation of the holding portion 48 is difficult to perform in a narrow body cavity under observation with the endoscope, and instability from a viewpoint of a manual operation is caused. The invention of the present reference embodiment has been developed in view of the above problem, and an object thereof is to provide a harvesting device for an endoscope configured to easily take a blood vessel and which is convenient for use.

Figure 14:
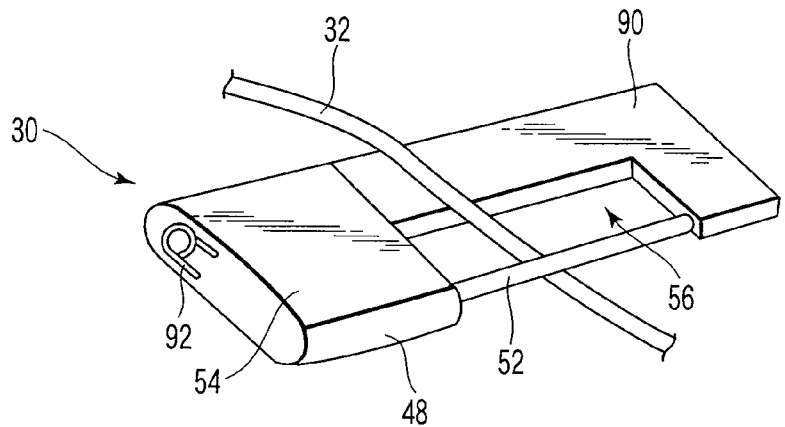
FIG. 14 is a perspective view showing a holding portion of a harvesting device for an endoscope according to a first reference embodiment of the present invention.

As shown in FIG. 14, the holding portion 48 of the harvesting device 30 for the endoscope according to the present reference embodiment has a substantially thin and long plate-like shape having a substantially rectangular take-in opening 56. Moreover, the holding portion 48 is formed by a substantially L-shaped thin plate-like holding portion board member 90 positioned on the proximal side and one side of the take-in opening 56, a substantially rectangular thin plate-like holding portion distal member 54 positioned on the distal side of the take-in opening 56, and a holding portion shaft 52 positioned on the other side of the take-in opening 56.

Figure 15A:
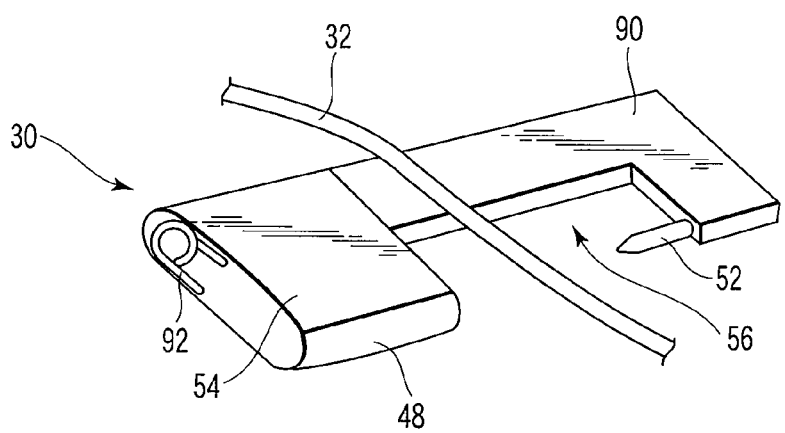
FIG. 15A is a perspective view showing the holding portion of the harvesting device for the endoscope in a state in which a holding portion distal member is disposed in a horizontal state according to the first reference embodiment of the present invention.
Figure 15B:
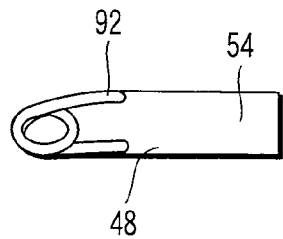
FIG. 15B is a front view showing the holding portion of the harvesting device for the endoscope in the state in which the holding portion distal member is disposed in the horizontal state according to the first reference embodiment of the present invention.

As shown in FIGS. 15A and 15B, in the same manner as in the first embodiment, the holding portion shaft 52 is configured to move forward and backward in the longitudinal axis direction of the harvesting device 30 for the endoscope. The distal end portion of the holding portion shaft 52 is configured to move between the closed position, in which the distal end portion is locked with the holding portion distal member 54 to bring the one side portion of the take-in opening 56 into the closed state, and the opened position in which the distal end portion is maximally moved to the proximal side to bring the one side portion of the take-in opening 56 into the opened state.

Figure 16A:
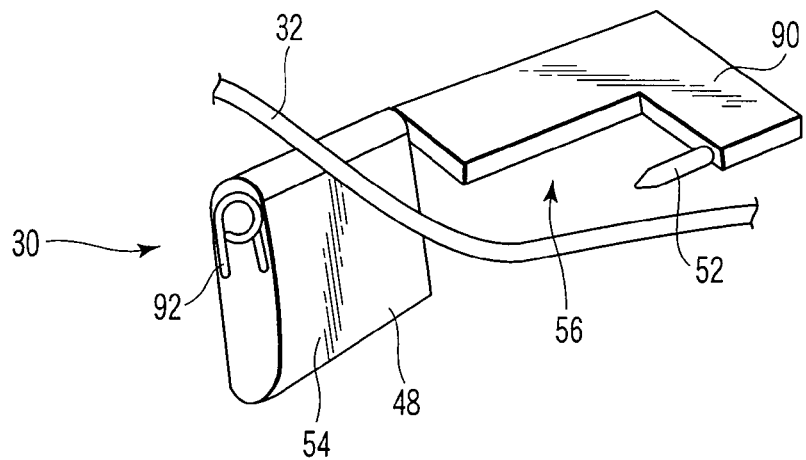
FIG. 16A is a perspective view showing the holding portion of the harvesting device for the endoscope in a state in which the holding portion distal member is in a rotated state according to the first reference embodiment of the present invention.
Figure 16B:
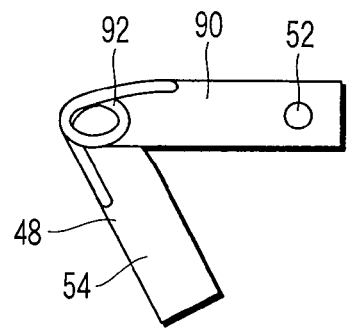
FIG. 16B is a front view showing the holding portion of the harvesting device for the endoscope in the state in which the holding portion distal member is in the rotated state according to the first reference embodiment of the present invention.

The holding portion distal member 54 is supported pivotally by a distal end portion of the holding portion board member 90 and configured to rotate around a rotary axis extending in the longitudinal axis direction of the harvesting device 30 for the endoscope, as shown in FIGS. 16A and 16B. Then, an elastic member 92 which urges the holding portion distal member 54 with respect to the holding portion board member 90 is interposed between the holding portion board member 90 and the holding portion distal member 54 so that the holding portion distal member 54 retains a horizontal state with respect to the holding portion board member 90. When a load is applied to the holding portion distal member 54, the holding portion distal member 54 is rotated with respect to the holding portion board member 90 to bring the distal end portion of the take-in opening 56 into an opened state. When the load is released from the holding portion distal member 54, through a function of the elastic member 92, the holding portion distal member 54 returns to the horizontal state with respect to the holding portion board member 90 to bring the distal end portion of the take-in opening 56 into a closed state.

Next, an operation of the harvesting device 30 for the endoscope of the present reference embodiment will be described. When the main blood vessel 32 is taken by the holding portion 48 under observation with the endoscope, the holding portion shaft 52 is moved backward to the proximal side to bring the one side portion of the take-in opening 56 into the opened state, and the holding member operating portion 46 is operated to arrange the main blood vessel 32 in the take-in opening 56. In this case, when the load is applied to the holding portion distal member 54 by the main blood vessel 32, the holding portion distal member 54 is rotated with respect to the holding portion board member 90 to bring the distal end portion of the take-in opening 56 into the opened state, so that the main blood vessel 32 can easily be arranged in the take-in opening 56. When the main blood vessel 32 is arranged in the take-in opening 56 and the load is released from the holding portion distal member 54, through the function of the elastic member 92, the holding portion distal member 54 is returned to the horizontal state with respect to the holding portion board member 90, and the distal end portion of the take-in opening 56 is brought into the closed state. Afterward, the holding portion shaft 52 is moved forward to the distal side, the distal end portion of the holding portion shaft 52 is locked with the holding portion distal member 54, and the one side portion of the take-in opening 56 is brought into the closed state to take the main blood vessel 32 into the take-in opening 56.

Therefore, the harvesting device 30 for the endoscope of the present reference embodiment produces the following effect. In the present embodiment, to arrange the main blood vessel 32 in the take-in opening 56, when the load is applied to the holding portion distal member 54 by the main blood vessel 32, the holding portion distal member 54 rotates to bring the distal end portion of the take-in opening 56 into the opened state. When the load on the holding portion distal member 54 by the main blood vessel 32 is released, through the function of the elastic member 92, the holding portion distal member 54 rotates to bring the distal end portion of the take-in opening 56 into the closed state. Therefore, the take-in of the main blood vessel 32 is facilitated, and thus convenience of the harvesting device 30 for the endoscope is improved.

Figure 17:
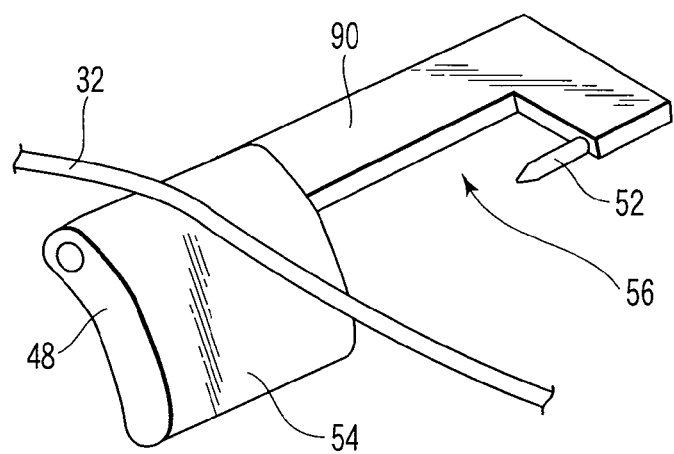
FIG. 17 is a perspective view showing a holding portion of a harvesting device for an endoscope according to a second reference embodiment of the present invention.

FIG. 17 shows a second reference embodiment of the present invention. A component having a function similar to that of the first reference embodiment is denoted with the same reference numerals, and description thereof is omitted. The holding portion distal member 54 of the present reference embodiment is formed of an elastic material, and fixed to the holding portion board member 90. In the harvesting device 30 for the endoscope of the present reference embodiment, when the load is applied to the holding portion distal member 54 by the main blood vessel 32, the holding portion distal member 54 is elastically deformed and curved to bring the distal end portion of the take-in opening 56 into the opened state. Then, when the load is released from the holding portion distal member 54, through elasticity of the holding portion distal member 54 itself, the holding portion distal member 54 is returned to the horizontal state with respect to the holding portion board member 90 to bring the distal end portion of the take-in opening 56 into the closed state. Therefore, the harvesting device 30 for the endoscope of the present reference embodiment produces an effect similar to that of the harvesting device 30 for the endoscope of the first reference embodiment.

Figure 18:
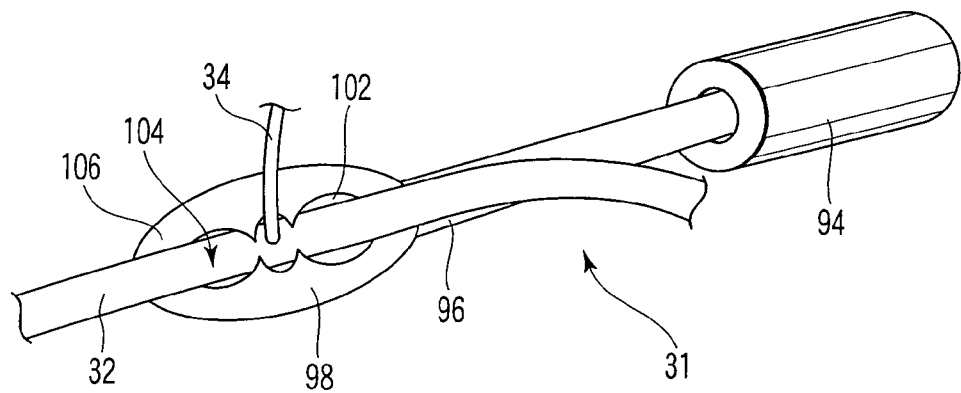
FIG. 18 is a perspective view showing a dissecting device for an endoscope according to a third reference embodiment of the present invention.
Figure 19:
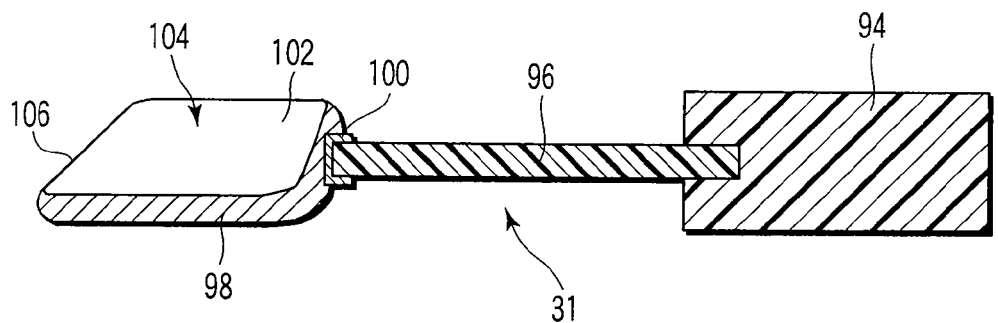
FIG. 19 is a longitudinal sectional view showing the dissecting device for the endoscope according to the third reference embodiment of the present invention.
Figure 27:
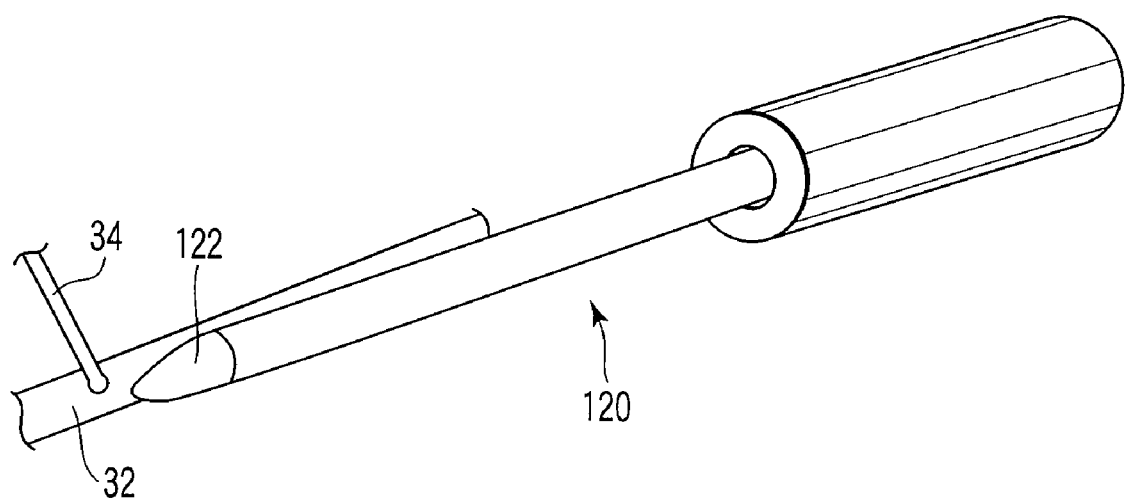
FIG. 27 is a perspective view showing a conventional dissecting device for an endoscope for dissecting a blood vessel.

FIGS. 18 and 19 show a third reference embodiment of the present invention. As shown in FIG. 27, in a conventional dissecting device 120 for an endoscope to dissect a main blood vessel 32 from a tissue, a spatulate head member 122 for dissecting the main blood vessel 32 is arranged at a distal end portion of the dissecting device, and this head member 122 is moved along the main blood vessel 32 in a longitudinal axis direction of the main blood vessel 32 to dissect the main blood vessel 32. However, the main blood vessel 32 has a circularly tubular shape. Therefore, to completely dissect the main blood vessel 32 from the tissue, while gradually moving the head member 122 in a peripheral direction of the main blood vessel 32, the head member has to be moved forward and backward in the longitudinal axis direction of the main blood vessel 32 many times, which complicates the dissecting operation. At a portion where a side branch blood vessel 34 is branched from the main blood vessel 32, a shape of a dissect portion is complicated, and hence the dissecting operation becomes difficult. The invention of the present reference embodiment has been developed in view of the above problem, and an object thereof is to provide a dissecting device for an endoscope configured to easily dissect the main blood vessel and which is convenient for use.

As shown in FIGS. 18 and 19, a dissecting device 31 for an endoscope of the present reference embodiment is formed by connecting a handle member 94 to be grasped by an operator, an elongated main body member 96 to be inserted into a body cavity and a head member 98 to dissect the main blood vessel 32 in order from a proximal side. It is to be noted that instead of the solid main body member 96, a hollow sheath member may be used. A distal end portion of the main body member 96 is connected to the head member 98 via a bush member 100, and the head member 98 is rotatable together with the bush member 100 around a longitudinal axis of the main body member 96.

In the head member 98, a dissecting portion 102 to receive the main blood vessel 32 slidably in a longitudinal axis direction of the main blood vessel 32 so as to cover the substantially whole periphery of an outer peripheral surface of the main blood vessel 32 is formed to pierce in the substantially above longitudinal axis direction. To pass the side branch blood vessel 34, the head member 98 is provided with a cutout portion 104 communicating the dissecting portion 102 with the outside and substantially extending over the whole length of the dissecting portion 102. Furthermore, on a distal side of the head member 98, a guide portion 106 continuously and smoothly connecting a distal end portion of the head member 98 to a distal end portion of the cutout portion 104 is formed so that the head member 98 is guided by the side branch blood vessel 34 to align the distal end portion of the cutout portion 104 with the side branch blood vessel 34.

Next, an operation of the dissecting device 31 for the endoscope of the present reference embodiment will be described. To dissect the main blood vessel 32 from the tissue, the main blood vessel 32 is received in the dissecting portion 102 of the head member 98, and the head member 98 is moved forward along the main blood vessel 32 in the longitudinal axis direction of the main blood vessel 32, whereby substantially the whole periphery of the outer peripheral surface of the main blood vessel 32 is dissected from the tissue. Then, at a portion where the side branch blood vessel 34 is branched from the main blood vessel 32, through the forward movement of the head member 98 along the main blood vessel 32 in the longitudinal axis direction of the main blood vessel 32, the guide portion 106 is abutted on the side branch blood vessel 34, the head member 98 is guided by the side branch blood vessel 34 to rotate with respect to the main body member 96, and the distal end portion of the cutout portion 104 is aligned with the side branch blood vessel 34. Then, while passing the side branch blood vessel 34 through the cutout portion 104, the head member 98 is moved forward to dissect substantially the whole periphery of the outer peripheral surface of the main blood vessel 32 from the tissue.

Therefore, the dissecting device 31 for the endoscope of the present reference embodiment produces the following effect. In the dissecting device 31 for the endoscope of the present reference embodiment, the main blood vessel 32 is received in the dissecting portion 102, the head member 98 is moved forward in the longitudinal axis direction of the main blood vessel 32 to dissect the outer peripheral surface of the main blood vessel 32 from the tissue, and the main blood vessel 32 can be dissected without the forward and backward movement of the head member 98 in the longitudinal axis direction of the main blood vessel 32 many times. At the portion where the side branch blood vessel 34 is disposed, the head member 98 is rotated around the longitudinal axis of the main blood vessel 32 to align the distal end portion of the cutout portion 104 with the side branch blood vessel 34. While passing the side branch blood vessel 34 through the cutout portion 104, the head member 98 is moved in the longitudinal axis direction of the main blood vessel 32, and the main blood vessel 32 can be dissected even at the portion where the side branch blood vessel 34 is disposed. Thus, the main blood vessel 32 can easily be dissected, and thus the convenience of the dissecting device 31 for the endoscope is improved.

Moreover, at the portion where the side branch blood vessel 34 is disposed, only through the forward movement of the head member 98 in the longitudinal axis direction of the main blood vessel 32, the guide portion 106 is abutted on the side branch blood vessel 34, the head member 98 is guided by the side branch blood vessel 34 to rotate with respect to the main body member 96, and the distal end portion of the cutout portion 104 is aligned with the side branch blood vessel 34. That is, the cutout portion 104 is automatically aligned with the side branch blood vessel 34, and thus the convenience of the dissecting device 31 for the endoscope is further improved.

Figure 20:
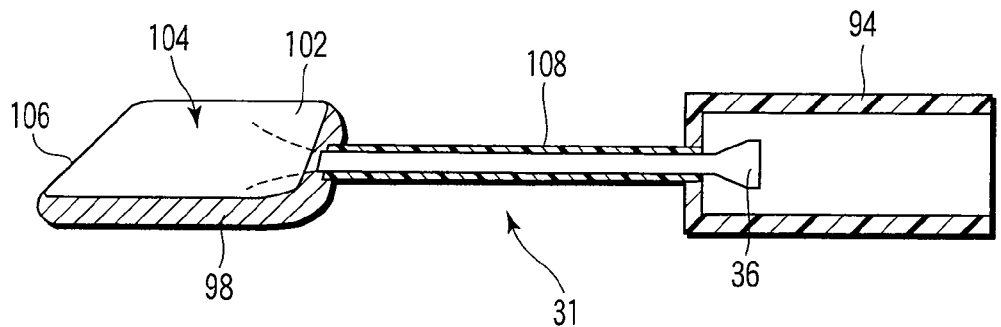
FIG. 20 is a longitudinal sectional view showing a dissecting device for an endoscope and an endoscope according to a fourth reference embodiment of the present invention.
Figure 21:
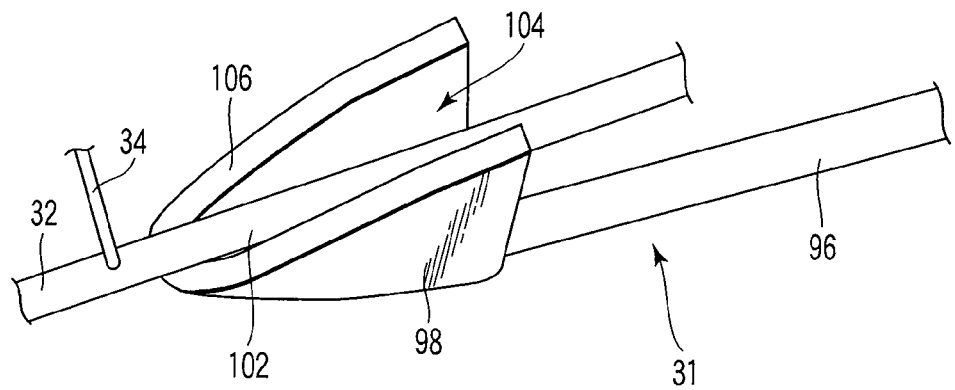
FIG. 21 is a perspective view showing a distal end portion of a dissecting device for an endoscope according to a fifth reference embodiment of the present invention.
Figure 22:
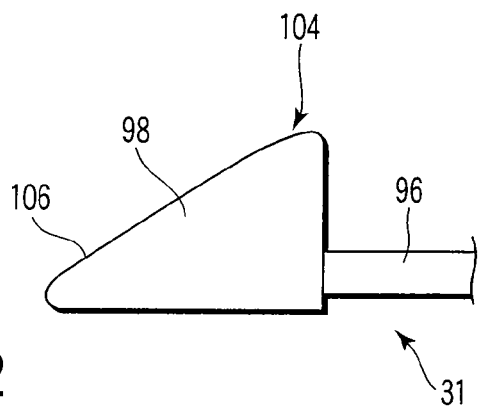
FIG. 22 is a side view showing the distal end portion of the dissecting device for the endoscope according to the fifth reference embodiment of the present invention.
Figure 23:
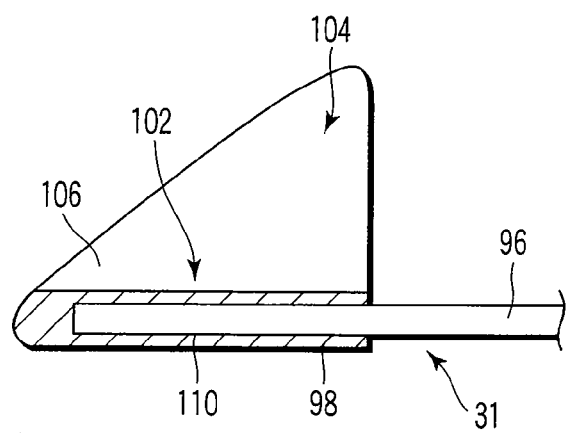
FIG. 23 is a longitudinal sectional view showing the distal end portion of the dissecting device for the endoscope according to the fifth reference embodiment of the present invention.
Figure 24:
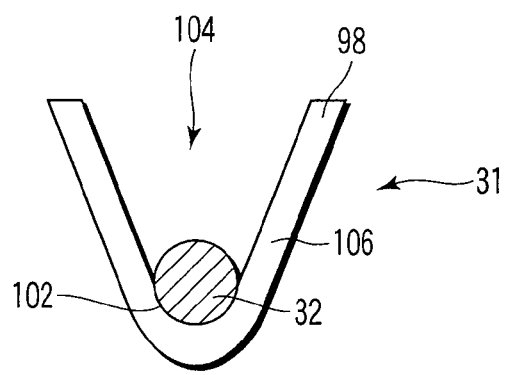
FIG. 24 is a transverse sectional view showing the distal end portion of the dissecting device for the endoscope according to the fifth reference embodiment of the present invention.

FIG. 20 shows a fourth reference embodiment of the present invention. A component having a function similar to that of the third reference embodiment is denoted with the same reference numerals, and description thereof is omitted. The handle member 94 of the present reference embodiment has a hollow shape opening on a proximal side, and a hollow sheath member 108 is used as a main body member. Then, an endoscope 36 is to be inserted from a proximal opening of the sheath member 108 via the proximal opening of the handle member 94 and inserted through the sheath member 108. Furthermore, the head member 98 is fixed to a distal end portion of the sheath member 108, and at least a part of the head member 98 is formed of a transparent material so that the distal side can be observed from a distal end portion of the endoscope 36 arranged at the distal end portion of the sheath member 108.

Next, an operation of the dissecting device 31 for the endoscope of the present reference embodiment will be described. To dissect the main blood vessel 32 from the tissue, at the portion where the side branch blood vessel 34 is disposed, the dissecting device 31 for the endoscope is operated and rotated by the handle member 94 under observation with the endoscope to rotate the head member 98, whereby the end of the cutout portion 104 is aligned with the side branch blood vessel 34. Therefore, the dissecting device 31 for the endoscope of the present reference embodiment produces an effect similar to that of the dissecting device 31 for the endoscope of the third reference embodiment. Unlike the dissecting device 31 for the endoscope of the third reference embodiment, the guide portion 106 is not abut on the side branch blood vessel 34, and therefore it is avoided that an unnecessary force is applied to the side branch blood vessel 34.

FIGS. 21 to 24 show a fifth reference embodiment of the present invention. A component having a function similar to that of the third reference embodiment is denoted with the same reference numerals, and description thereof is omitted. The head member 98 of the present reference embodiment has a shape in which two substantially right-angled triangular plate-like members are connected at bottom side portions so that right-angled portions are disposed on a proximal side and the plate-like members form a predetermined angle, and the head member has a V-shape as viewed from a distal side. Moreover, the head member 98 is provided with an insertion hole 110 from the proximal side to the distal side at a bottom portion of the V-shape, and the distal end portion of the main body member 96 is inserted into this insertion hole 110. Furthermore, the head member 98 is configured to rotate around the longitudinal axis of the main body member 96 with respect to the main body member 96. In the head member 98 of the present embodiment, the dissecting portion 102 is formed by an inner bottom portion of the V-shape, and the cutout portion 104 is formed by an upward opening shape of the V-shape. Oblique line portions of two plate-like members have a smooth slope shape to form the guide portion 106. A function and an effect of a dissecting device 31 for an endoscope of the present reference embodiment are similar to those of the third reference embodiment.

Figure 25:
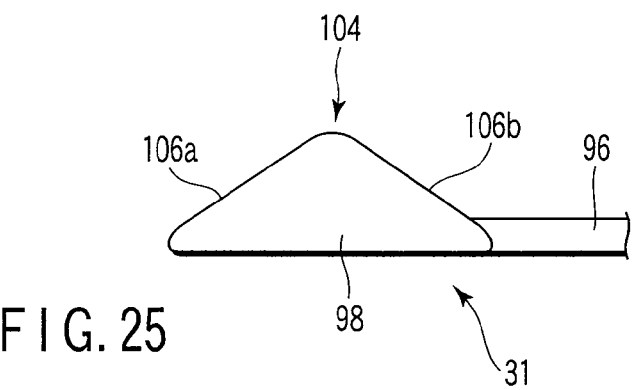
FIG. 25 is a side view showing a distal end portion of a dissecting device for an endoscope according to a sixth reference embodiment of the present invention.

FIG. 25 shows a sixth reference embodiment of the present invention. A component having a function similar to that of the fifth reference embodiment is denoted with the same reference numerals, and description thereof is omitted. A head member 98 of the present reference embodiment is provided with a first guide portion 106a on the distal side and a second guide portion 106b on the proximal side. This second guide portion 106b has a shape which gently separate from the longitudinal axis of the main body member 96 from the proximal side to the distal side. In the dissecting device 31 for the endoscope of the present reference embodiment, even at the portion where the side branch blood vessel 34 is branched from the main blood vessel 32, through either forward or backward movement of the head member 98, the main blood vessel 32 can be easily dissect from the tissue, and thus convenience of the dissecting device 31 for the endoscope is further improved.

Figure 26:
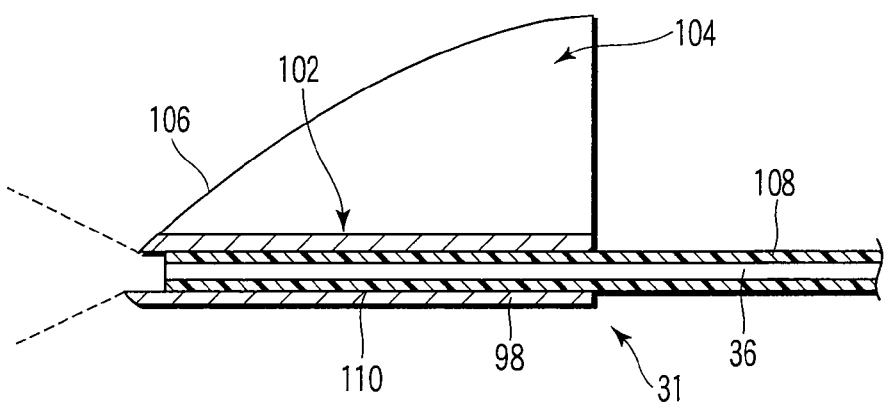
FIG. 26 is a longitudinal sectional view showing a distal end portion of a dissecting device for an endoscope according to a seventh reference embodiment of the present invention.

FIG. 26 shows a seventh reference embodiment of the present invention. A component having a function similar to that of the fifth reference embodiment is denoted with the same reference numerals, and description thereof is omitted. In the present reference embodiment, in the same manner as in the fourth reference embodiment, the hollow sheath member 108 through which the endoscope 36 is to be inserted is used as the main body member. The insertion hole 110 of the head member 98 extends through the member from the proximal side to the distal side, and the distal side can be observed via a distal end portion of the insertion hole 110 from the distal end portion of the endoscope 36 arranged at the distal end portion of the sheath member 108. A function and an effect of the dissecting device 31 for the endoscope of the present reference embodiment are similar to those of the fourth reference embodiment.

Reference aspects of the present invention will hereinafter be enumerated.

In the first reference aspect of the present invention, a harvesting device for an endoscope is characterized by comprising an elongated main body member (an outer tube member) including a distal end portion and a proximal end portion; a catching portion (a holding portion) arranged at the distal end portion of the main body member and provided with a take-in opening to take in a blood vessel; an opening and closing member (a holding portion shaft) provided at the catching portion and configured to move to open and close a part of an outer peripheral portion of the take-in opening; an opening and closing member operating portion (a holding portion shaft operating portion) provided at the proximal end portion of the main body member and to move the opening and closing member; a rotary member (a holding portion distal member) provided at the catching portion and configured to rotate to open and close the other part of the outer peripheral portion of the take-in opening; and elastic mechanism for urging the rotary member so that the rotary member retains a state in which the rotary member closes the other part of the outer peripheral portion of the take-in opening.

In this harvesting device for the endoscope, the one part of the outer peripheral portion of the take-in opening is opened through the movement of the opening and closing member by the opening and closing member operating portion, the blood vessel is arranged in a take-in opening, the one part of the outer peripheral portion of the take-in opening is closed through the movement of the opening and closing member by the opening and closing member operating portion, and the blood vessel is taken into the take-in opening. In the arrangement of the blood vessel into the take-in opening, when a load is applied to the rotary member by the blood vessel, the rotary member is rotated to open the other part of the outer peripheral portion of the take-in opening. When the load on the rotary member due to the blood vessel is released, through a function of an elastic member, the rotary member rotates to close the other part of the outer peripheral portion of the take-in opening.

In the second reference aspect of the present invention, the harvesting device for the endoscope according to the first reference aspect is characterized in that the elastic mechanism is an elastic member.

In this harvesting device for the endoscope, the elastic member urges the rotary member so that the rotary member retains a state in which the rotary member closes the other part of the outer peripheral portion of the take-in opening.

In the third reference aspect of the present invention, the harvesting device for the endoscope according to the first reference aspect is characterized in that the elastic mechanism is the elasticity of the rotary member itself.

In this harvesting device for the endoscope, the elasticity of the rotary member itself urges the rotary member so that the rotary member retains a state in which the rotary member closes the other part of the outer peripheral portion of the take-in opening.

According to the harvesting device for the endoscope of the first to third reference aspects of the present invention, the blood vessel can easily be taken, and hence convenience of the harvesting device for the endoscope is improved.

In the fourth reference aspect of the present invention, a dissecting device for an endoscope is characterized by comprising an elongated main body member including a distal end portion, and a head member provided at the distal end portion of the main body member and to dissect a main blood vessel, wherein the head member includes a dissecting portion to receive the main blood vessel slidably in a longitudinal axis direction of the main blood vessel so as to cover an outer peripheral surface of the main blood vessel, and a cutout portion communicating the dissecting portion with the outside substantially over the whole length of the dissecting portion.

In this dissecting device for the endoscope, the main blood vessel is received in the dissecting portion, and the head member is moved in the longitudinal axis direction of the main blood vessel. At a portion where a side branch blood vessel is disposed, the head member is rotated around the longitudinal axis of the main blood vessel to align an end of the cutout portion with the side branch blood vessel, and while passing the side branch blood vessel through the cutout portion, the head member is moved in the longitudinal axis direction of the main blood vessel. In this way, the outer peripheral surface of the main blood vessel is dissected from a tissue.

In a fifth reference aspect of the present invention, the dissecting device for the endoscope according to the fourth reference aspect is characterized in that the head member is connected to the main body member and configured to rotate around a longitudinal axis of the main body member and includes at least one guide portion provided at the head member and continuously and smoothly connected to the end of the cutout portion.

In this dissecting device for the endoscope, at the portion where the side branch blood vessel is disposed, through the movement of the head member in the longitudinal axis direction of the main blood vessel, the guide portion is abutted on the side branch blood vessel, and the head member is guided by the side branch blood vessel to rotate with respect to the main body member, whereby the end of the cutout portion is aligned with the side branch blood vessel.

In the sixth reference aspect of the present invention, the dissecting device for the endoscope according to the fifth reference aspect is characterized in that the main body member is a sheath member wherein the endoscope is inserted through the sheath member and a distal side is observable with the endoscope from a distal end portion of the endoscope, and this dissecting device for the endoscope further includes a handle member provided at a proximal end portion of the sheath member and to operate and rotate the dissecting device for the endoscope around a longitudinal axis of the sheath member.

In this dissecting device for the endoscope, at the portion where the side branch blood vessel is disposed, the dissecting device for the endoscope is operated and rotated by the handle member under observation with the endoscope to rotate the head member, whereby the end of the cutout portion is aligned with the side branch blood vessel.

In a seventh reference aspect of the present invention, the dissecting device for the endoscope according to the fifth or sixth aspect is characterized in that the at least one guide portion is comprised of two guide portions connected to both ends of the cutout portion, respectively.

In this dissecting device for the endoscope, one of the two guide portions is abutted on the side branch blood vessel, and one of both the ends of the cutout portion is aligned with the side branch blood vessel.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cutting device for an endoscope comprising:
an elongated outer tube member through which an endoscope is to be inserted and including a distal end portion where a distal end portion of the endoscope is to be arranged and a proximal end portion where a proximal end portion of the endoscope is to be arranged;
a cutting member inserted through the outer tube member, including a cutting portion arranged at the distal end portion of the outer tube member and to perform a cutting, and configured to move so that the cutting member moves the cutting portion between a cutting position where the cutting portion is to perform the cutting and a standby position where the cutting portion is to perform no cutting through a switching position between the cutting position and the standby position;
an operating portion to move the cutting member;
a wipe member inserted through the outer tube member, including a wipe portion arranged at the distal end portion of the outer tube member, and configured to move so that the wipe member moves the wipe portion to wipe the distal end portion of the endoscope; and
a conversion mechanism configured to convert the movement of the cutting member into a movement of the wipe member to interlock a cutting movement of the cutting portion with a wiping movement of the wipe portion when the cutting member moves the cutting portion between the standby position and the switching position and not to convert a movement of the cutting member into a movement of the wipe member when the cutting member moves the cutting portion between the switching position and the cutting position.

2. The cutting device for the endoscope according to claim 1, wherein
the outer tube member extends in an axial direction,
the cutting member extends in the axial direction, and configured to move in the axial direction relative to the outer tube member so that the cutting member moves the cutting portion between a distal cutting position and a proximal standby position,
the wipe member extends in the axial direction, and configured to rotate about a central axis of the wipe member relative to the outer tube member so that the wipe member rotates the wipe portion to wipe the distal end portion of the endoscope,
the conversion mechanism includes;
a first converting engaging portion provided on a proximal end portion of the cutting member and configured to be moved in the axial direction by an axial movement of the cutting member,
a first engaging member including a second converting engaging portion, wherein the second converting engaging portion is configured to be engaged with the first converting engaging portion and interacted with the first converting engaging portion to convert the axial movement of the cutting member into a rotational movement of the first engaging member when the cutting member moves the cutting portion between the standby position and the switching position and not to engage with the first converting engaging portion when the cutting member moves the cutting portion between the switching position and the cutting position, and including a first transmitting engaging portion;
a second engaging member including a second transmitting engaging portion, wherein the second transmitting engaging portion is engaged with the first transmitting engaging portion and configured to be interacted with the first transmitting engaging portion to convert the rotational movement of the first engaging member into a rotational movement of the second engaging member, provided on a proximal end portion of the wiping member, and configured to rotate the wipe member by the rotational movement of the second engaging member.

3. The cutting device for the endoscope according to claim 1, wherein
the outer tube member extends in an axial direction,
the cutting member extends in the axial direction, and configured to move in the axial direction toward a first and a second axial orientation opposite to each other relative to the outer tube member so that the cutting member moves the cutting portion between the distal cutting position and the proximal standby position,
the wipe member extends in the axial direction, and configured to rotate about a central axis of the wipe member toward a first and a second rotational orientation opposite to each other relative to the outer tube member so that the wipe member rotates the wipe portion to wipe the distal end portion of the endoscope,
the conversion mechanism includes:
a first converting cam portion provided on a proximal end portion of the cutting member and configured to be moved in the axial direction by an axial movement of the cutting member; and
a cam member provided on a proximal end portion of the wiping member, configured to rotate the wipe member by a rotational movement of the cam member and including a second converting cam portion wherein the second converting cam portion is configured to be contacted with the first converting cam portion and interacted with the first converting cam portion to convert an axial movement of the cutting member toward the first axial orientation into a rotational movement of the cam member toward the first rotational orientation when the cutting member moves the cutting portion between the standby position and the switching position and separated from the first converting cam portion when the cutting member moves the cutting portion between the switching position and the cutting position; and
an urging member urging the cam member toward the second rotational orientation.

* * * * *